US 6,652,723 B1

(12) United States Patent
Nadanami et al.

(10) Patent No.: US 6,652,723 B1
(45) Date of Patent: Nov. 25, 2003

(54) HYDROGEN GAS SENSOR

(75) Inventors: Norihiko Nadanami, Aichi (JP);
Norobu Ishida, Gifu (JP); Takafumi Oshima, Aichi (JP); Ryuji Inoue, Gifu (JP); Tomonori Kondo, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 186 days.

(21) Appl. No.: 09/716,225

(22) Filed: Nov. 21, 2000

(30) Foreign Application Priority Data

Nov. 24, 1999 (JP) .......................................... 11-333422
Oct. 6, 2000 (JP) ...................................... 2000-307375

(51) Int. Cl.[7] .......................................... G01N 27/407
(52) U.S. Cl. ...................... 204/424; 204/425; 204/426
(58) Field of Search ................................ 204/415, 424, 204/425, 426, 428, 429, 432; 205/783.5, 793; 73/23.31

(56) References Cited

U.S. PATENT DOCUMENTS 4,718,991 A * 1/1988 Yamazoe et al. ........... 204/410
6,337,009 B1 * 1/2002 Nadanami et al. .......... 204/424

FOREIGN PATENT DOCUMENTS

JP 7-31153 4/1995
JP 8-327592 12/1996

OTHER PUBLICATIONS

Translation of JP 8–327592A, Inaba et al, Dec. 1996.*
Logothetis et al High–Temperature Oxygen Sensors Based on Electrochemical Oxygen PUmping, ACS Symposium Series 309, pp. 136–154, 1986.*
Bard & Faulkner, "Electrochemical Methods", pp. 22–26, 1980.*

* cited by examiner

Primary Examiner—Nam Nguyen
Assistant Examiner—Kaj K. Olsen
(74) Attorney, Agent, or Firm—Sughrue Mion, PLLC (57) ABSTRACT

A hydrogen gas sensor capable of accurately measuring hydrogen concentration of a measurement gas atmosphere in the presence of a variety of interfering gasses such as $H_2O$ and CO. In the hydrogen gas sensor, the flow sectional area of a diffusion-rate limiting portion 6 is rendered small; the electrode surfaces of first and second electrodes 3 and 4 are rendered large; and/or a solution containing a polymer electrolyte which may be identical to that of a proton-conductive layer 2 is applied onto the surfaces of the first and second electrodes 3 and 4 to thereby form a layer containing the polymer electrolyte. Thus, the rate of conduction of protons from the first electrode 3 to the second electrode 4 becomes greater than the rate at which protons are derived from hydrogen which is introduced onto the first electrode 3 via the diffusion-rate limiting portion 6.

20 Claims, 6 Drawing Sheets

HYDROGEN GAS SENSOR

BACKGROUND OF THE INVENTION

1. Field of the Invention

The present invention relates to a hydrogen gas sensor, and more particularly, to a hydrogen gas sensor suitable for measuring the hydrogen concentration of a fuel gas used for fuel cells.

2. Description of the Related Art

In view of the issue of global-scale environmental deterioration, fuel cells, which are clean and efficient power sources, have recently become the subject of active studies. Among fuel cells, a polymer electrolyte fuel cell (PEFC) is expected to be suitable for vehicle use due to its advantages, including low operation temperature and high output density. In this case, a reformed gas obtained from methanol or the like is advantageously used as a fuel gas. Further, in order to improve efficiency and other parameters of performance, a gas sensor capable of directly measuring hydrogen concentration of the reformed gas is needed.

Since such a hydrogen gas sensor is used in a hydrogen-rich atmosphere, the operation temperature of the gas sensor must be low (about 100° C. or less). Such a low-operation-temperature-type sensor is disclosed in Japanese Patent Publication (kokoku) No. 7-31153. In the sensor, a working electrode, a counter electrode, and a reference electrode are disposed on an insulating substrate, and the three electrodes are integrally covered with a gas-permeable, proton-conductive film; more specifically, "NAFION®" (trademark, product of Dupont), which is a type of fluororesin. NAFION® is a proton-conductive material capable of operating at low temperature and is used at portions of polymer electrolyte fuel cells.

The present Inventors found that when NAFION® is used as a proton-conductive layer as in the gas sensor disclosed in Japanese Patent Publication No. 7-31153, the sensor output varies depending on the $H_2O$ concentration partial pressure of a gas under measurement (hereinafter referred to as a measurement gas atmosphere), so that accurate measurement becomes difficult. Further, the present Inventors found that the above phenomena occurs because protons pass through NAFION® together with $H_2O$ molecules, and therefore, the proton conductivity varies with the $H_2O$ concentration of the measurement gas atmosphere. That is, when the proton-conductive layer is formed of NAFION®, the sensor output depends on the $H_2O$ concentration of the measurement gas atmosphere, so that the sensor output decreases greatly, especially when the $H_2O$ concentration is low.

The present Inventors further found that although porous Pt electrodes (catalysts) are generally known to exhibit high activity at low temperature (porous Pt electrodes are used, for example, in fuel cells), when such a Pt electrode is exposed to an atmosphere having a high CO concentration, CO is adsorbed on the Pt electrode, or the Pt electrode is CO-poisoned, so that the sensor output is greatly decreased.

Since many fuel cells use pressurized fuel gas in order to improve power generation efficiency, sensors used in the fuel gas are required to have a small pressure dependency. However, in the sensor described in the above-mentioned Japanese Patent Publication No. 7-31153, a gas under measurement is diffused to the working electrode via the gas-permeable, proton-conductive film, so that the sensor exhibits a great pressure dependency, depending on the structure of the proton-conductive film itself, and therefore high measurement accuracy cannot be obtained.

SUMMARY OF THE INVENTION

It is therefore an object of the present invention to provide a hydrogen gas sensor capable of accurately measuring hydrogen concentration in the presence of a variety of interfering gasses.

In the hydrogen gas sensor of the present invention, the rate of conduction of protons from a first electrode to a second electrode is rendered greater than the rate at which protons are derived from hydrogen introduced onto the first electrode via a diffusion-rate limiting portion.

That is, because the rate of conduction of protons from the first electrode to the second electrode is sufficiently greater than the rate at which protons are derived from hydrogen introduced from the measurement gas atmosphere onto the first electrode via the diffusion-rate limiting portion, the sensor can accurately measure hydrogen concentration without causing a great decrease in sensor output. That is so even when the measurement gas atmosphere has a low $H_2O$ concentration or a high CO concentration.

The present invention is applicable to both a hydrogen gas sensor not having a reference electrode and to a hydrogen gas sensor having a reference electrode. In the latter gas sensor, the voltage applied between the first and second electrodes can be variably controlled such that a constant voltage is produced between the first electrode and the reference electrode, or such that the hydrogen concentration on the first electrode becomes constant. Therefore, for any given hydrogen concentration an optimal voltage can be applied between the first and second electrodes, so that a more accurate measurement of hydrogen concentration can be obtained within a wide range of concentration.

The hydrogen gas sensor according to the present invention is advantageously used for measuring an atmosphere in which hydrogen $H_2O$, and other components coexist, especially for measuring the hydrogen concentration of a fuel gas for polymer electrolyte fuel cells.

In a preferred mode of the present invention, the diffusion-rate limiting portion preferably has a relatively high gas-diffusion resistance, so as to render the proton-conducting performance excessive. In this case, the rate of conduction of protons through the proton-conductive layer becomes greater than the rate at which protons are derived from hydrogen introduced onto the first electrode. The gas-diffusion resistance of the diffusion-rate limiting portion is increased, for example, by increasing the length (thickness) of the diffusion-rate limiting portion in the gas diffusion direction or by decreasing the cross sectional area perpendicular to the gas diffusion direction (hereinafter referred to as a "flow sectional area"). Alternatively, when the diffusion-rate limiting portion is formed of a porous material, the gas-diffusion resistance of the diffusion-rate limiting portion is increased by decreasing the porosity (pore diameter, apparent porosity, etc.) of the porous material.

The gas-diffusion resistance of the diffusion-rate limiting portion is preferably set as follows in order to render the rate of conduction of protons from the first electrode to the second electrode greater than the rate at which protons derived from hydrogen are introduced onto the first electrode via the diffusion-rate limiting portion.

(1) Proton Conduction Condition A

A proton-conducting rate under severe conditions is measured. That is, a current (a) flowing between the first and second electrodes is measured upon applying a sufficiently high voltage between the first and second electrodes in a state in which the gas-diffusion resistance of the diffusion-rate limiting portion is rendered sufficiently small (e.g., about 0.9 mA/mm$^2$ or more of the first electrode (3), with current conversion, at $H_2$=40%) in order to introduce a sufficiently large amount of hydrogen onto the first electrode, but under the severest conditions for proton conduction; e.g., conditions such that the measurement gas atmosphere has a very low $H_2O$ concentration (specifically, 10% or less at 80° C.) or a very high CO concentration (specifically, 1000 ppm or greater). Although the above-described current (a) need not be a saturation current, the applied voltage (specifically, 50 mV or higher) is preferably equal to or higher than the voltage applied in the case of condition B described below.

(2) Proton Conduction Condition B

Figure 2:
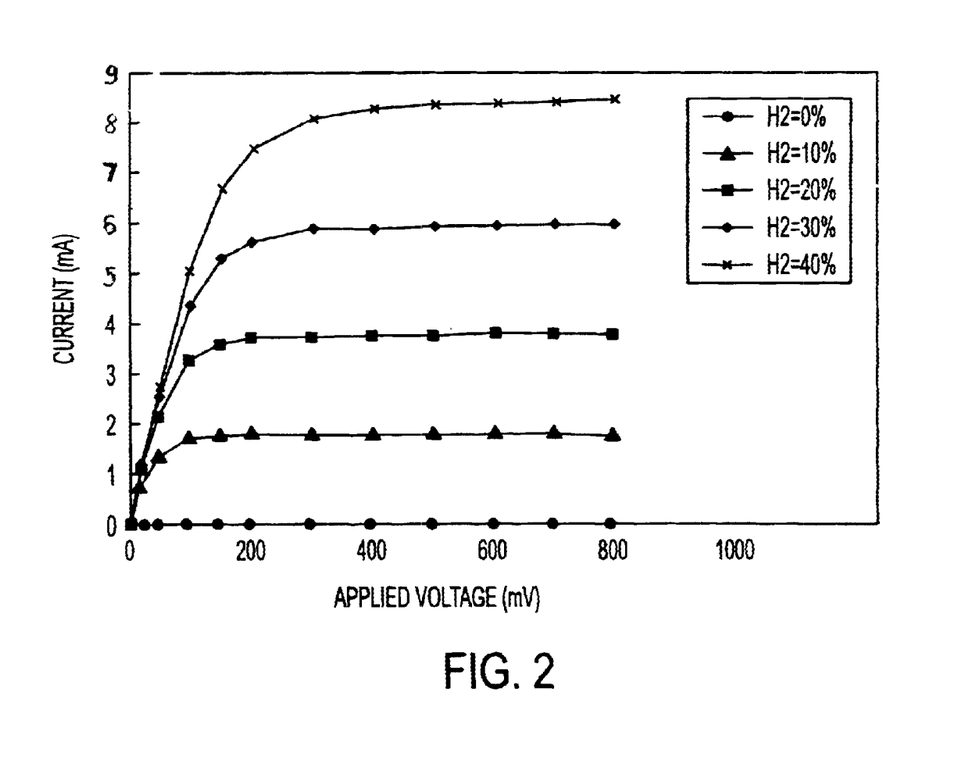
FIG. 2 is a graph of the results of measurement 1, showing an applied voltage-current characteristic for each of various hydrogen concentrations.

Next, a proton-conducting rate under favorable conditions is measured. That is, a saturation current (b) flowing between the first and second electrodes is measured upon application of a sufficiently high voltage between the first and second electrodes in a state in which the gas-diffusion resistance of the diffusion-rate limiting portion is rendered larger (e.g., less than about 0.9 mA/mm$^2$ of the first electrode (3), with current conversion, at $H_2$=40%) in order to sufficiently reduce the amount of hydrogen introduced onto the first electrode, but under favorable conditions for proton conduction, e.g., conditions such that the measurement gas atmosphere has a sufficiently high $H_2O$ concentration (specifically, 15% or greater, more preferably 20% or greater, at 80° C.) or a sufficiently low CO concentration (specifically, 800 ppm or less). The sufficiently high voltage for producing a saturation current (b) is 300 mV or more at $H_2$=40%, and varies according to the $H_2$ concentration as shown in FIG. 2. In the case of $H_2$=10%, it is about 100 mV or more.

(3) Setting of Gas-diffusion Resistance

When the gas-diffusion resistance of the diffusion-rate limiting portion is set to a sufficiently high value under condition B, current (a)>saturation current (b). Thus, the hydrogen gas sensor is configured such that proton-conducting rate (current value) under the severest conditions for proton conduction>proton-conducting rate under favorable conditions for proton conduction. In this hydrogen sensor, the proton-conducting rate is always greater than the proton-generation rate corresponding to the rate at which hydrogen is introduced onto the first electrode (or the largest proton-generation rate corresponding to the largest rate at which hydrogen is introduced onto the first electrode).

In yet another preferred mode of the present invention, current (c) flowing between the first and second electrodes is measured under severe conditions for proton conduction; current (d) flowing between the first and second electrodes is measured under favorable conditions for proton conduction; and the gas-diffusion resistance of the diffusion-rate limiting portion is set such that the ratio of current (d) to current (c) (=current (d)/current (c)) or its reciprocal (=current (c)/current (d)) approaches 1. As a result, the $H_2O$-concentration dependency and CO-concentration dependency of the current flowing through the first and second electrodes decrease. Preferably, the gas-diffusion resistance of the diffusion-rate limiting portion and/or the area of the first or second electrode is properly set, or a predetermined polymer electrolyte solution is applied to the interface of the first or second electrode which is in contact with the proton-conductive layer, such that the ratio (saturation current flowing between the first and second electrodes at $H_2O$=30%)/(saturation current flowing between the first and second electrodes at $H_2O$=10%) falls within the range of 1 to 1.5, preferably 1 to 1.15, more preferably, 1 to 1.1, most preferably, 1 to 1.05. Further, preferably the gas-diffusion resistance of the diffusion-rate limiting portion and/or the area of the first or second electrode is appropriately set, or a polymer electrolyte solution is applied to the interface of the first or second electrode which is in contact with the proton-conductive layer, such that the ratio (saturation current flowing between the first and second electrodes at CO=1000 ppm)/(saturation current flowing between the first and second electrodes at CO=0 ppm) falls within the range of 0.9 to 1 (the reciprocal of the rate falls within the range of 1 to 1.1), more preferably, 0.95 to 1 (the reciprocal of the rate falls within the range of 1 to 1.05). Thus, a layer containing a polymer electrolyte is formed at the interface.

In a preferred mode of the present invention, the first and second electrodes are formed in an opposed manner to sandwich the proton-conductive layer. This structure reduces the resistance between the first and second electrodes to thereby improve the proton-conducting performance of the proton-conductive layer. However, when the gas-diffusion resistance of the diffusion-rate limiting portion is excessively high, the sensitivity of the hydrogen gas sensor is lowered. Therefore, the area of at least one of the first and second electrodes is preferably increased when the sensor must have a relatively high sensitivity. Further, the first and second electrodes may be formed on the same plane of the proton-conductive layer, if a sufficient degree of sensitivity can be achieved.

In a preferred mode of the present invention, a solution containing a polymer electrolyte identical to that of the proton-conductive layer is applied to the side of each electrode in contact with the proton-conductive layer (the interface between each electrode and the proton-conductive layer). This increases the contact area between the proton-conductive layer and catalytic components carried on the electrode, so that the proton-conducting performance is further increased. Further, the proton-conducting performance may be enhanced by decreasing the thickness of the proton-conductive layer.

In a preferred mode of the present invention, the proton-conductive layer is a polymer electrolytic proton-conductive layer which sufficiently operates at a relatively low temperature, for example, at temperatures not greater than 150° C., preferably, at temperatures not greater than 130° C., more preferably, at around 80° C.; e.g., a proton-conductive layer formed of a resin-based solid polymer electrolyte.

In a preferred mode of the present invention, a proton-conductive layer is formed of one or more types of fluororesins, more preferably of "NAFION®" (trademark, product of Dupont).

In a preferred mode of the present invention, each electrode is a porous electrode formed of carbon or another suitable material, and carries a catalyst such as Pt on the side of the electrode in contact with the proton-conductive layer.

In the preferred mode of the present invention, the proton-conductive layer, the respective electrodes, and the diffusion-rate limiting portion are supported on a support to thereby constitute an integrated hydrogen gas sensor. The support is formed of an inorganic insulating material such as an alumina ceramic or an organic insulating material such as resin. Further, the diffusion-rate limiting portion is preferably formed of a porous alumina ceramic or a like material having gas permeability, or alternatively may be formed of small holes each having a small flow sectional area, such as one or more through-holes each having a very small opening diameter, which are formed at a portion of the support formed of a dense body. Such fine through-holes can be formed by use of, for example, laser machining or ultrasonic machining. In the case of laser machining, the opening diameter may be adjusted by controlling the irradiation diameter, output power, time, etc., of a laser beam. The average pore diameter of the porous material and the opening diameter of the through-holes are preferably not less than 1 μm. In this case, since gas diffusion proceeds outside the region of Knudsen diffusion, the pressure dependency of the sensor can be lowered.

The hydrogen gas sensor of the present invention can be fabricated by physically sandwiching the proton-conductive layer and the respective electrodes between two supports such that the respective electrodes contact the proton-conductive layer. Alternatively, the respective electrodes may be bonded to the proton-conductive layer by hot pressing.

In the preferred mode of the present invention, a hydrogen gas sensor not having a reference electrode has a support for supporting the proton-conductive layer, the first electrode, the second electrode and the diffusion-rate limiting portion, and a hydrogen gas sensor provided with a reference electrode has a support for supporting the proton-conductive layer, the first electrode, the second electrode, the reference electrode and the diffusion-rate limiting portion.

Reference numerals are used in the drawings to identify the following:

1a, 1b: upper and lower supports
2: proton-conductive layer
3: first electrode
4: second electrode
5: reference electrode
6: diffusion-rate limiting portion
7: power source
8: ammeter
9: power source
10: voltmeter
11: aperture

DESCRIPTION OF THE PREFERRED EMBODIMENTS

Embodiments of the present invention will be described with reference to the drawings in order to clarify the above-described preferred mode of the present invention. However, the present invention should not be construed as being limited thereto.

Figure 1:
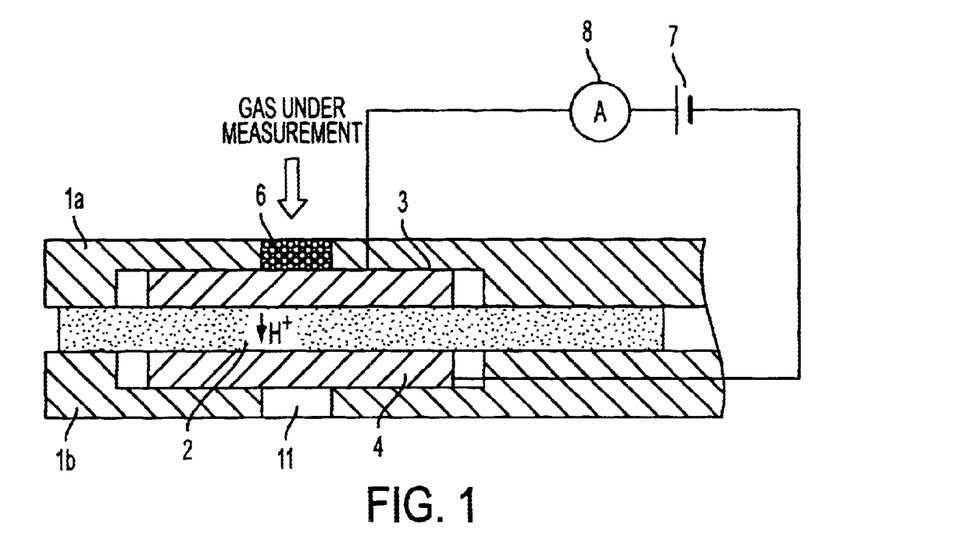
FIG. 1 is a sectional view of a main portion of a hydrogen gas sensor according to the present invention.

First, the structure of a hydrogen gas sensor according to the present invention will be described. FIG. 1 is a sectional view of a main portion of the hydrogen gas sensor. As shown in FIG. 1, in the hydrogen gas sensor, a first electrode 3 and a second electrode 4 are disposed on opposite surfaces, respectively, of a proton-conductive layer 2 such that the first electrode 3 and the second electrode 4 sandwich the proton-conductive layer 2. Further, an upper support 1a and a lower support 1b sandwich the first electrode 3 and the second electrode 4. A diffusion-rate limiting portion 6 is formed in the upper support 1a located above the first electrode 3. The diffusion-rate limiting portion 6 located between the first electrode 3 and a measurement gas atmosphere, and the second electrode 4 contacts the measurement gas atmosphere via an aperture 11 formed in the lower support 1b.

A series circuit comprising a power source 7 and an ammeter 8 is connected between the first and second electrodes 3 and 4 via lead portions, so that a voltage is applied between the first and second electrodes 3 and 4, and current flowing between the first and second electrodes 3 and 4 can be measured.

Next, the measurement principle of the hydrogen gas sensor will be described with reference to FIG. 1.

(1) Hydrogen having reached the first electrode 3 via the gas-diffusion-rate limiting portion 6 is dissociated into protons by virtue of the catalytic action of a catalytic component such as Pt carried on the first electrode 3 and the voltage applied between the first electrode 3 and the second electrode 4.

(2) The protons thus generated are conducted to the second electrode 4 via the proton-conductive layer 2 and are converted to hydrogen (gas) on the second electrode 4, which hydrogen diffuses into the measurement gas atmosphere via the aperture 11. When the applied voltage is sufficiently high such that a saturation current flows between the first electrode 3 and the second electrode 4, the current flowing between the first electrode 3 and the second electrode 4 varies in proportion to the hydrogen concentration. Therefore, the hydrogen concentration can be measured by detecting the saturation current using ammeter 8.

Measurement of hydrogen concentration was performed using the above-described hydrogen gas sensor (see FIG. 1). In the hydrogen gas sensor, the proton-conductive layer was formed of NAFION®; the first and second electrodes were porous carbon electrodes carrying a catalyst such as Pt on the side in contact with the proton-conductive layer; the support was formed of dense alumina ceramic; and the diffusion-rate limiting portion was formed of porous alumina ceramic.

Measurement 1

For each of various hydrogen concentrations (hydrogen concentrations of a gas under measurement), current flowing between the first and second electrodes 3 and 4 was measured, while the voltage applied between the first and second electrodes 3 and 4 was varied. Measurement conditions were as follows.

Measurement Conditions

Gas composition: $H_2$ (0–40%), $CO_2$ (15%), $H_2O$ (25%), $N_2$ (bal.);

Gas temperature: 80° C.;

Gas flow rate: 4 l/min; and

Applied voltage: 0–800 mV.

Next, results of the measurement will be described. FIG. 2 is a graph showing an applied voltage/current characteristic for each of various hydrogen concentrations. As shown in FIG. 2, a saturation current flows when the applied voltage exceeds about 400 mV, and the magnitude of the saturation current varies in proportion to the hydrogen concentration of the measurement gas. Therefore, the hydrogen concentration can be measured using the hydrogen gas sensor.

Embodiment 1, Measurement 2

Next, with reference to the following measurement results, an example method of rendering the rate of conduction of protons from the first electrode to the second electrode greater than the rate at which hydrogen is introduced onto the first electrode via the diffusion-rate limiting portion is described, as well as the effect thereof.

Measurement 2-1

The structure of hydrogen gas sensors used in the present measurement will be described. Hydrogen gas sensors having the above-described structure (see FIG. 1) but differing from one another in terms of gas-diffusion resistance of the diffusion-rate limiting portion were fabricated. Specifically, the cross sectional area of the diffusion-rate limiting portion as measured perpendicular to the gas diffusion direction was changed among the hydrogen gas sensors. The same voltage was applied between the first and second electrodes 3 and 4 of each hydrogen gas sensor, and the current flowing between the first and second electrodes 3 and 4 was measured. The measurement conditions were as follows.

Gas composition: $H_2$ (40%), $CO_2$ (15%), $H_2O$ (20%), $N_2$ (bal.);

Gas temperature: 80° C.;

Gas flow rate: 4 l/min; and

Applied voltage: 800 mV.

Figure 3:
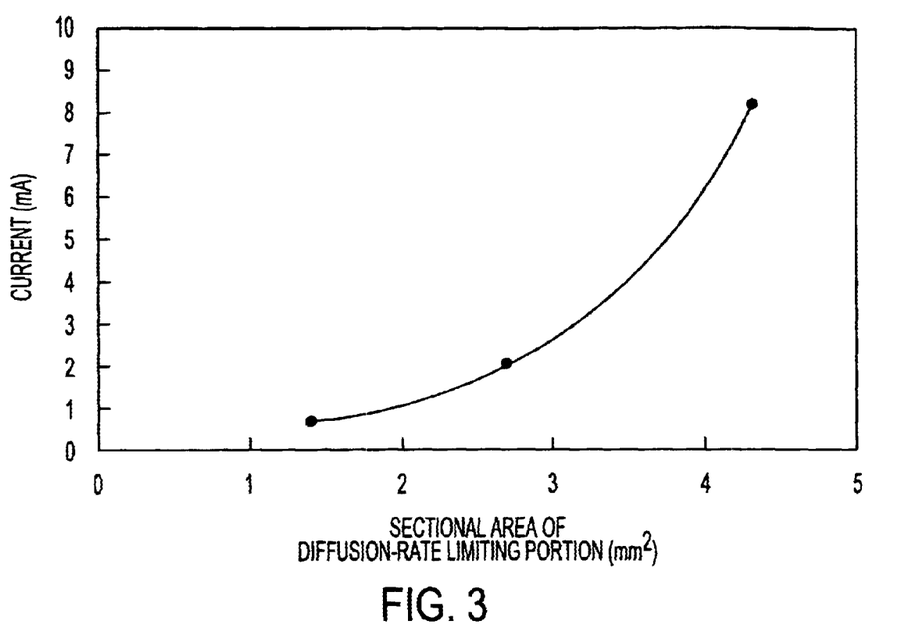
FIG. 3 is a graph of the results of measurement 2-1, showing the relationship between flow sectional area of the diffusion-rate limiting portion and current (sensitivity) at $H_2=40\%$.

Next, the results of the measurement will be described. FIG. 3 is a graph showing the relationship between the flow sectional area of the diffusion-rate limiting portion and current (sensitivity) at $H_2$=40%. As shown in FIG. 3, the current decreases with the flow sectional area of the diffusion-rate limiting portion, and therefore, the amount of hydrogen introduced onto the first electrode can be reduced by increasing in the gas-diffusion resistance of the diffusion-rate limiting portion.

Measurement 2-2

At each of various $H_2O$ concentrations, a measurement similar to measurement 2-1 was performed using the gas sensors of measurement 2-1. The measurement conditions were as follows.

Gas composition: $H_2$ (40%), $CO_2$ (15%), $H_2O$ (10, 20, 30%), $N_2$ (bal.);

Gas temperature: 80° C.;

Gas flow rate: 4 l/min; and

Applied voltage: 800 mV.

Figure 4:
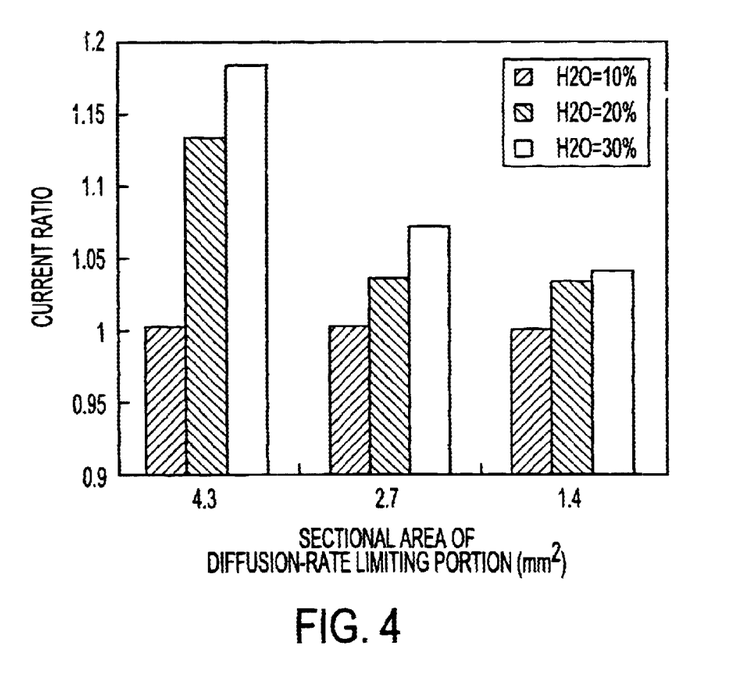
FIG. 4 is a graph of the results of measurement 2-2, showing the dependency of current (sensitivity) on flow sectional area (gas-diffusion resistance) of the diffusion-rate limiting portion and $H_2O$ concentration.

FIG. 4 is a graph describing the results of measurement 2-2 and showing the dependency of current (sensitivity) on the flow sectional area (gas-diffusion resistance) of the diffusion-rate limiting portion and $H_2O$ concentration. Since the absolute value of current (sensitivity) varies with the flow sectional area, each of currents (sensitivities) at $H_2O$= 20% and 30% is represented as a ratio to current (sensitivity) at $H_2O$=10%. The absolute values of the respective currents are shown in Table 1.

TABLE 1

| $H_2O$ concentration | Current (Absolute value) (mA) Sectional area of Diffusion-rate limiting portion | | |
|---|---|---|---|
| | 4.3 mm$^2$ | 2.7 mm$^2$ | 1.4 mm$^2$ |
| 10% (c) | 7.316 (a) | 2.097 | 0.665 |
| 20% | 8.296 | 2.173 | 0.688 |
| 30% (d) | 8.671 | 2.247 | 0.693 (b) |

(a) Current under proton conduction condition A; i.e., low gas-diffusion resistance of the diffusion-rate limiting portion, and severe conditions for proton conduction;

(b) Current under proton conduction condition B; i.e., high gas-diffusion resistance of the diffusion-rate limiting portion, and favorable conditions for proton conduction;

(c) Severe conditions for proton conduction; and (d) Favorable conditions for proton conduction.

As shown in FIG. 4, the $H_2O$-concentration dependency decreases with the flow sectional area of the diffusion-rate limiting portion. Therefore, when the gas-diffusion resistance of the diffusion-rate limiting portion is increased to thereby render the proton-conductive performance excessive relative to the proton generation rate, the $H_2O$-concentration dependency of the sensitivity or detection output of the sensor can be reduced. Further, Table 1 demonstrates that since current (a)>current (b), the rate of conduction of protons from the first electrode to the second electrode is greater than the rate at which protons are derived from hydrogen which is introduced onto the first electrode via the diffusion-rate limiting portion. Further, as shown in FIG. 4, for $H_2O$=30%, the current ratio (current (d)/current (c)) was 1.185 when the sectional area of the diffusion-rate limiting portion was 4.3 mm$^2$, 1.071 when the sectional area was 2.7 mm , and 1.041 when the sectional area was 1.4 mm$^2$.

Measurement 2-3

The CO-concentration dependency of current (sensitivity) was investigated using the gas sensors of measurement 2-2. Specifically, at each of various CO concentrations, a measurement similar to measurement 2-2 was performed. The measurement conditions were as follows.

Gas composition: $H_2$ (40%), $CO_2$ (15%), $H_2O$ (25%), CO (0, 1000 ppm), $N_2$ (bal.);

Gas temperature: 80° C.;

Gas flow rate: 4 l/min; and

Applied voltage: 800 mV.

Figure 5:
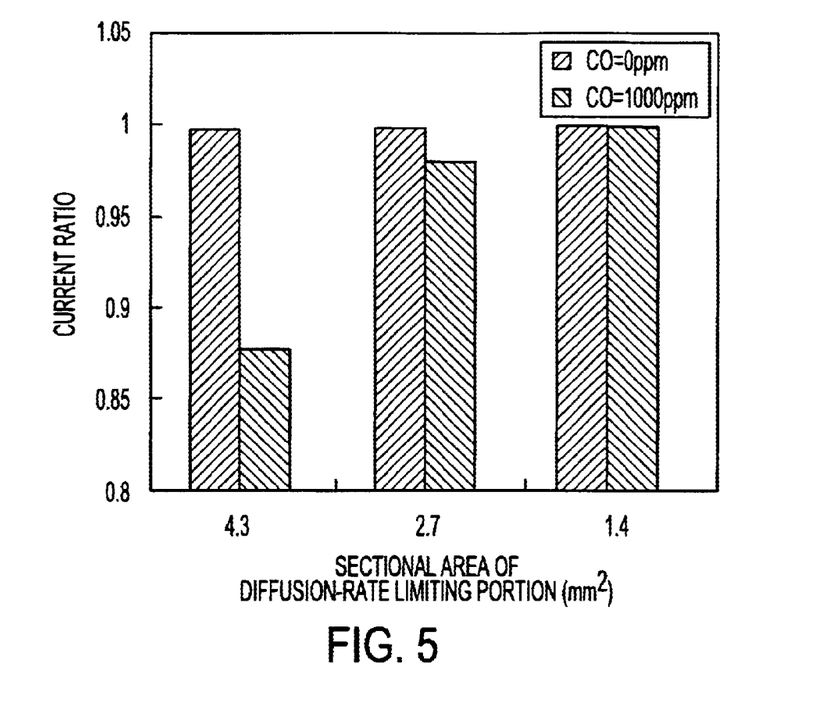
FIG. 5 is a graph of the results of measurement 2-3, showing the dependency of current (sensitivity) on flow sectional area (gas-diffusion resistance) of the diffusion-rate limiting portion and CO concentration.

FIG. 5 is a graph describing the results of measurement 2-3 and showing the dependency of current (sensitivity) on the flow sectional area (gas-diffusion resistance) of the diffusion-rate limiting portion and CO concentration. Since the absolute value of current (sensitivity) varies with the flow sectional area, current (sensitivity) at CO=1000 ppm is represented as a ratio to current (sensitivity) at CO=0 ppm.

As shown in FIG. 5, the CO-concentration dependency decreases with a decrease in the flow sectional area of the diffusion-rate limiting portion. Therefore, when the gas-diffusion resistance of the diffusion-rate limiting portion is increased to thereby render the proton-conductive performance excessive relative to the proton generation rate, the influence of CO-poisoning of Pt serving an electrode catalyst can be reduced. Further, as shown in FIG. 5, the current ratio (current (c: CO=1000 ppm)/current (d: CO=0 ppm)) was 0.8785 (the reciprocal was 1.138) when the sectional area of the diffusion-rate limiting portion was 4.3 mm$^2$, 0.9813 (the reciprocal was 1.019) when the sectional area was 1.4 mm$^2$.

As described above, since the gas-diffusion resistance of the diffusion-rate limiting portion is increased to thereby render the proton-conductive performance excessive relative to the proton generation rate, the influence, for example, of $H_2O$ and CO present in a measurement gas atmosphere can be reduced, thereby enabling a more accurate measurement of hydrogen concentration. The above-described method of increasing the gas-diffusion resistance is a mere example, and the gas-diffusion resistance may be increased by increasing the length of the diffusion-rate limiting portion with respect to the gas diffusion direction or by decreasing the pore diameter or porosity (open-pore ratio) of the porous material that constitutes the diffusion-rate limiting portion.

Embodiment 2, Measurement 3

Next, an example method in which the proton-conducting performance itself is improved in order to render the rate of conduction of protons from the first electrode to the second electrode greater than the rate at which hydrogen gas is introduced onto the first electrode is described.

The structure of hydrogen gas sensors used in the present measurement will next be described. Hydrogen gas sensors having the above-described structure (see FIG. 1) but differing from one another in terms of the areas of the first and second electrodes were fabricated. A measurement similar to measurement 2-2 was performed using the thus-fabricated hydrogen gas sensors.

Figure 6:
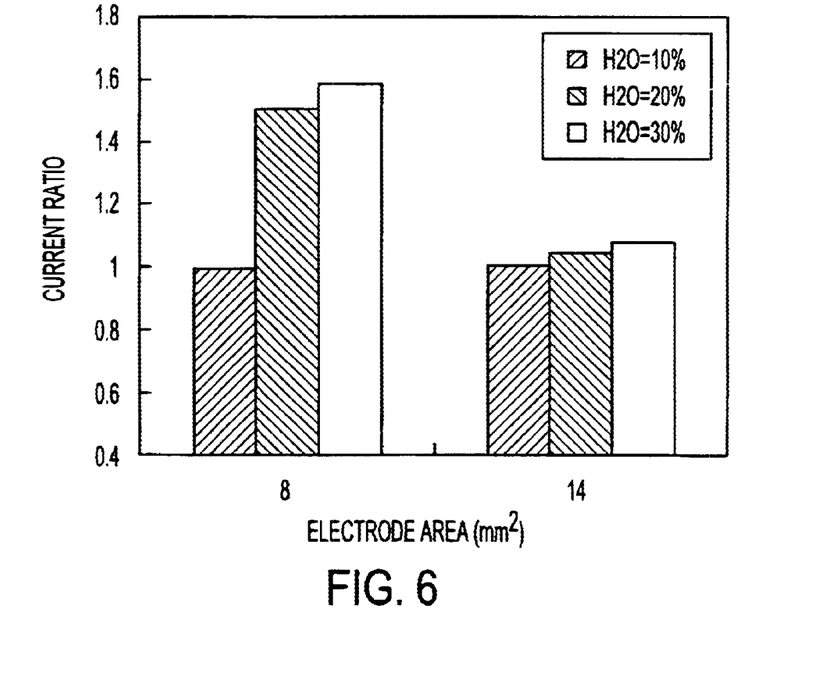
FIG. 6 is a graph of the results of measurement 3, showing the dependency of current (sensitivity) on electrode area and $H_2O$ concentration.

FIG. 6 is a graph for describing the results of measurement 3 and showing the dependency of current (sensitivity) on electrode area and $H_2O$ concentration. For each electrode area, each of currents (sensitivities) at $H_2O$=20% and 30% is represented as a ratio to current (sensitivity) at $H_2O$=10%.

As shown in FIG. 6, when the electrode area is about doubled, the proton-conducting performance is improved, so that the $H_2O$-concentration dependency of the gas sensor sensitivity can be greatly reduced.

Embodiment 3, Measurement 4

Next, an example method in which a solution containing a polymer electrolyte that constitutes the proton-conductive layer is applied to the sides of the first or second electrode which are in contact with the proton-conductive layer (at the interfaces) is described, in order to improve the proton-conducting performance itself, whereby the rate of conduction of protons from the first electrode to the second electrode is rendered greater than the rate at which hydrogen is introduced onto the first electrode.

The structure of hydrogen gas sensors used in the present measurement will next be described. Hydrogen gas sensors were fabricated which had the above-described structure (see FIG. 1) and in which a mixed solution of NAFION® (5 wt. %), water, and an aliphatic lower alcohol was applied to the sides of the first or second electrode in contact with the proton-conductive layer, as well as hydrogen gas sensors which had the above-described structure and in which the mixed solution was not applied. The resistance between the first and second electrodes was measured at each of various $H_2O$ concentrations using the thus-fabricated hydrogen gas sensors. The measurement conditions were as follows. The area of the first electrode was the same as that of the second electrode.

Gas composition: $H_2$ (40%), $CO_2$ (15%), $H_2O$ (10–30%), $N_2$ (bal.);
Gas temperature: 80° C.;
Gas flow rate: 4 l/min; and
Resistance between first and second electrode: applied voltage (50 mV)/current.

Figure 7:
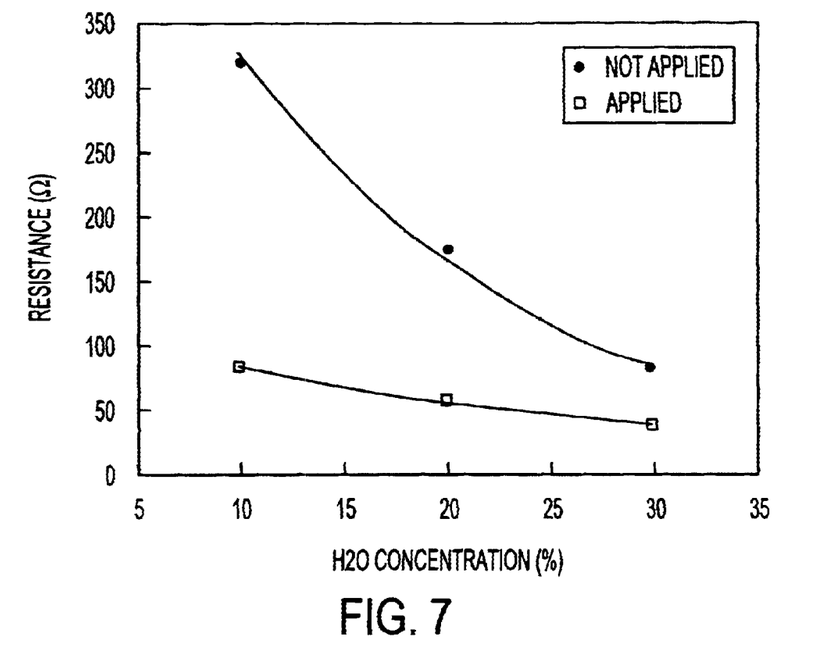
FIG. 7 is a graph of the results of measurement 4, showing the relationship between $H_2O$ concentration and resistance between the first and second electrodes for the case where a solution of a polymer electrolyte was applied, and for the case where the solution was not applied.

FIG. 7 is a graph describing the results of measurement 4 and showing the relationship between $H_2O$ concentration and resistance between the first and second electrodes for the case where the solution was applied and for the case where the solution was not applied. The resistance between the first and second electrodes was determined from current that flowed upon application of 50 mV.

As shown in FIG. 7, when a solution containing a predetermined polymer electrolyte is applied onto the electrode surface, the contact area between the proton-conductive layer and the electrodes increases, so that within a wide range of $H_2O$ concentration, the resistance between the first and second electrodes can be reduced to thereby improve the proton-conducting performance.

As described above, since a solution containing a predetermined polymer electrolyte is applied onto the electrode surface to thereby render the proton-conductive performance excessive, the influences, for example, of $H_2O$ and CO present in a measurement gas atmosphere can be reduced, thereby enabling a more accurate measurement of hydrogen concentration.

Further, the results of measurements 2–4 demonstrate that when the flow sectional area of the diffusion-rate limiting portion and the electrode surface of the first and second electrodes are optimized and a solution containing a polymer electrolyte is applied onto the electrode surface, the proton-conductive performance is improved in both relative and absolute terms, so that hydrogen concentration can be measured more accurately.

Figure 8:
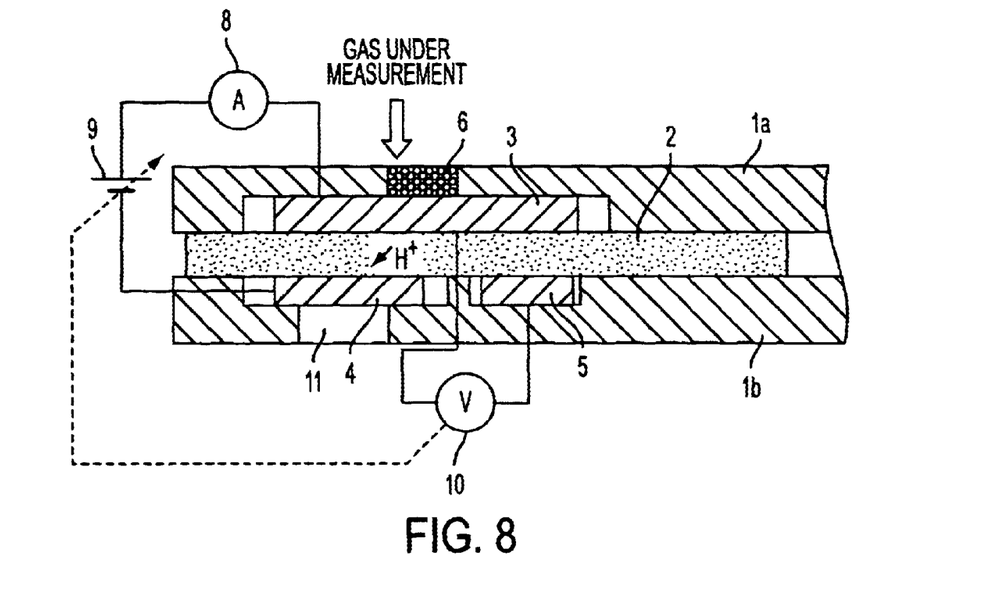
FIG. 8 is a sectional view of a main portion of another hydrogen gas sensor of the present invention.

Next, the structure of another hydrogen gas sensor according to the present invention will be described. This second hydrogen gas sensor differs from the hydrogen gas sensor shown in FIG. 1 in that it further includes a reference electrode. FIG. 8 is a sectional view of a main portion of the second hydrogen gas sensor. In FIG. 8, elements having the same functions as those shown in FIG. 1 are denoted by the same reference numerals.

As shown in FIG. 8, in the second hydrogen gas sensor, a first electrode 3 and a second electrode 4 are disposed on opposite surfaces, respectively, of a proton-conductive layer 2 such that the first electrode 3 and the second electrode 4 sandwich the proton-conductive layer 2. A reference electrode 5 is formed on the surface of the proton-conductive layer 2 on which the second electrode 4 is formed. Further, an upper support 1a and an lower support 1b sandwich the first electrode 3, the second electrode 4, and the reference electrode 5. A diffusion-rate limiting portion 6 is formed in the upper support 1a located above the first electrode 3. The diffusion-rate limiting portion 6 is provided between the first electrode and a measurement gas atmosphere, and the second electrode 4 is in contact with the measurement gas atmosphere via an aperture 11 formed in the lower support 1b. The reference electrode 5 is formed such that the reference electrode 5 is in contact with the proton-conductive layer 2 and is not exposed directly to a measurement gas atmosphere. The reference electrode 5 provides a reference potential.

A series circuit comprising a power source 9 and an ammeter 8 is connected between the first and second electrodes 3 and 4 via lead portions, so that a voltage is applied between the first and second electrodes 3 and 4, and current flowing between the first and second electrodes 3 and 4 can be measured. A voltmeter 10 is connected between the first electrode 3 and the reference electrode 5 via lead portions. Further, a control circuit is formed between the voltmeter 10 and the power source 9 in order to variably control the voltage applied between the first and second electrodes 3 and 4 in accordance with the potential difference between the first electrode 3 and the reference electrode 5.

Next, the measurement principle of the hydrogen gas sensor having a reference electrode will be described with reference to FIG. 8.

(1) When hydrogen reaches the first electrode 3 via the gas-diffusion-rate limiting portion 6, an electromotive force corresponding to the hydrogen concentration is generated between the first electrode 3 and the reference electrode 5 across the proton-conductive layer 2.

(2) A control voltage is applied between the first electrode 3 and the second electrode 4 such that the hydrogen concentration on the first electrode 3 becomes constant; i.e., the potential difference between the first electrode 3 and the reference electrode 5 becomes constant.

(3) The hydrogen having reached the first electrode 3 via the gas-diffusion-rate limiting portion 6 is dissociated into protons by virtue of the catalytic action of the catalytic component, such as Pt, carried on the first electrode 3 and the voltage applied between the first electrode 3 and the second electrode.

(4) The protons thus generated are conducted to the second electrode 4 via the proton-conductive layer 2 and are converted to hydrogen on the second electrode 4, which hydrogen diffuses into the measurement gas atmosphere via the aperture 11. When the above-described voltage applied in a controlled manner is sufficiently high so that a saturation current flows between the first electrode 3 and the second electrode 4, the current flowing between the first electrode 3 and the second electrode 4 varies in proportion to the hydrogen concentration. Therefore, the hydrogen concentration can be measured by detecting the saturation current using ammeter 8.

Since the voltage applied between the first and second electrodes 3 and 4 is controlled such that the hydrogen concentration on the first electrode 3 is maintained constant, a high voltage can be applied when the hydrogen concentration of the gas under measurement is high, and low voltage can be applied when the hydrogen concentration of the gas under measurement is low. In other words, an optimal voltage can be applied between the first and second electrodes 3 and 4 in accordance with hydrogen concentration. Further, in the gas sensor having the reference electrode (see FIG. 8), when the resistance between the first and second electrodes 3 and 4 increases for some reason, the applied voltage automatically changes properly, or can be changed properly. Therefore, hydrogen concentration can be measured accurately, while the influence of $H_2O$ and the like is further suppressed.

Embodiment 4, Measurement 5

Next, the results of measurement performed using the hydrogen gas sensor having a reference electrode (see FIG. 8) will be described. In the hydrogen gas sensor, the proton-conductive layer was formed of NAFION®; the first and second electrodes and the reference electrode were porous carbon electrodes carrying a catalyst such as Pt on the side in contact with the proton-conductive layer; the support was formed of dense alumina ceramic; and the diffusion-rate limiting portion was formed of porous alumina ceramic.

Further, in order to stabilize the hydrogen concentration on the reference electrode, the reference electrode was employed as a self-generation reference electrode. Specifically, a constant small current was caused to flow from the first electrode to the reference electrode to thereby supply protons to the reference electrode, whereby a portion of hydrogen generated on the reference electrode was leaked to the outside via a predetermined leakage resistance portion (small hole).

Moreover, as in the above-described embodiments 1 to 3, the flow sectional area of the diffusion-rate limiting portion and the electrode surface of the first and second electrodes were optimized, and a solution containing a polymer electrolyte was applied onto the surfaces of the first and second electrodes in contact with the proton-conductive layer, so that that the proton-conductive performance was improved in both relative and absolute terms. Specifically, the flow sectional area of the diffusion-rate limiting portion was set to 1.4 $mm^2$, the electrode area of the first electrode was set to 14 $mm^2$, and the electrode area of the second electrode was set to 10 $mm^2$.

For each of various $H_2O$ concentrations ($H_2O$ concentrations of a gas under measurement), the current flowing between the first and second electrodes was measured, while hydrogen concentration was varied. The measurement conditions were as follows.

Figure 9:
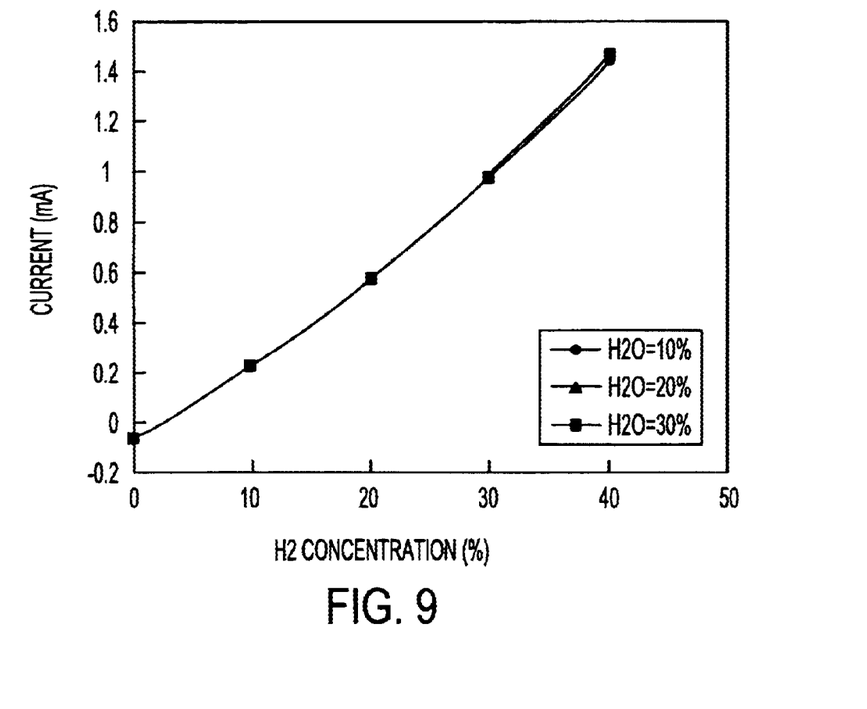
FIG. 9 is a graph of the results of measurement 5, showing the relationship between hydrogen concentration and current (current flowing between the first and second electrodes) at each of different $H_2O$ concentrations.
Figure 10:
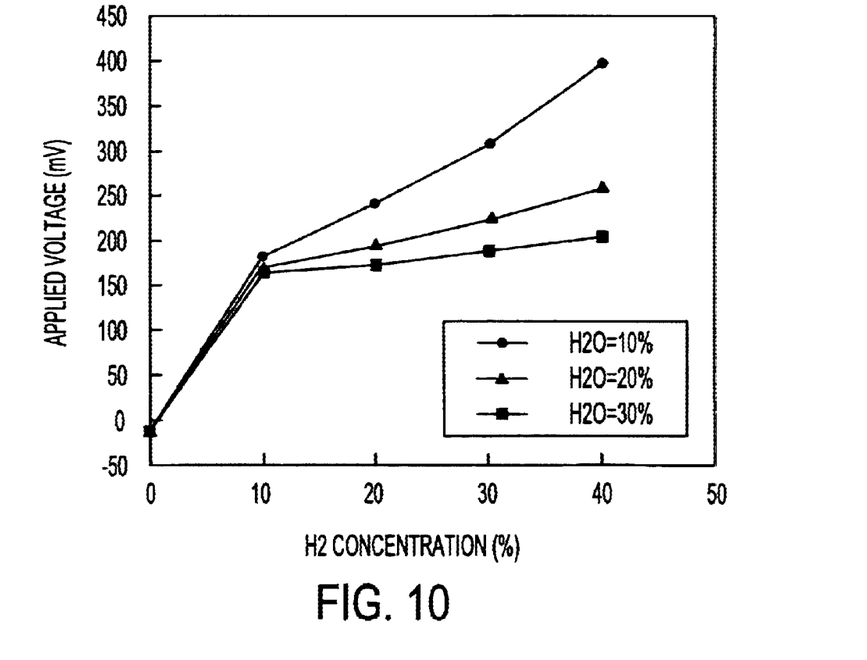
FIG. 10 is a graph of the results of measurement 5, showing the relationship between hydrogen concentration and applied voltage at each of different $H_2O$ concentrations.

Gas composition: $H_2$(0–40%), $CO_2$(15%), $H_2O$ (10–30%), $N_2$ (bal.);

Gas temperature: 80° C.;

Gas flow rate: 4 L/min;

Potential difference between first electrode and reference electrode (control target): 150 mV; and Constant current for self-generation reference electrode: 10 μA FIG. 9 is a graph describing the results of measurement 5 and showing the relationship between hydrogen concentration and current (current flowing between the first and second electrodes) at each of different $H_2O$ concentrations. FIG. 10 shows the voltage (control voltage applied between the first and second electrodes) at that time.

As shown in FIG. 9, current curves for different $H_2O$ concentrations become substantially identical over a wide range of hydrogen concentration. This indicates that when a reference electrode is used and the rate of proton conduction between the first and second electrodes is render sufficiently high, accurate measurement of hydrogen concentration becomes possible, while the influence of $H_2O$, etc. is reduced.

As shown in FIG. 10, the voltage applied between the first and second electrodes varies with hydrogen concentration, and the applied voltage increases as $H_2O$ concentration decreases. Therefore, provision of the reference electrode enables application of an optimal voltage between the first and second electrodes even when the conditions of a measurement gas atmosphere; e.g., gas composition, varies.

Embodiment 5, Measurement 6

Next the results of measurement will be described in which the gas pressure dependency of the hydrogen gas sensor having a reference electrode (see FIG. 8) was measured by use of hydrogen gas sensors whose diffusion-rate limiting portions had different pore diameters (opening diameters). Since Embodiment 5 is the same as Embodiment 4 excepting points which will be described in detail below, a repeated description will be omitted.

The diffusion-rate limiting portion of each sensor was constituted of a porous alumina ceramic having an average pore diameter of 0.31 $\mu$m or 1 $\mu$m or a dense alumina ceramic having through-holes each having an opening diameter of 30 $\mu$m, 50 $\mu$m, or 70 $\mu$m. The pore diameter and the opening diameter were measured through observation using a scanning electron microscope (SEM). A measurement gas was supplied under a different gas pressure to each of the hydrogen gas sensors whose diffusion-rate limiting portions had different pore or opening diameters, and the current flowing between the first and second electrodes was measured. Since the absolute value of the current varied depending on the pore diameter (opening diameter) of the diffusion-rate limiting portion, a ratio of the current at a pressure of 2.5 atm to that at a pressure of 1 atm was measured as a current ratio. The smaller the current ratio, the smaller the evaluated gas pressure dependency. The measurement conditions were as follows.

Gas composition: $H_2$ (40%), $CO_2$ (15%), $H_2O$ (15%), $N_2$ (bal.);

Gas temperature: 80° C.;

Gas flow rate: 4 L/min;

Gas pressure: 1 atm, 2.5 atm

Figure 11:
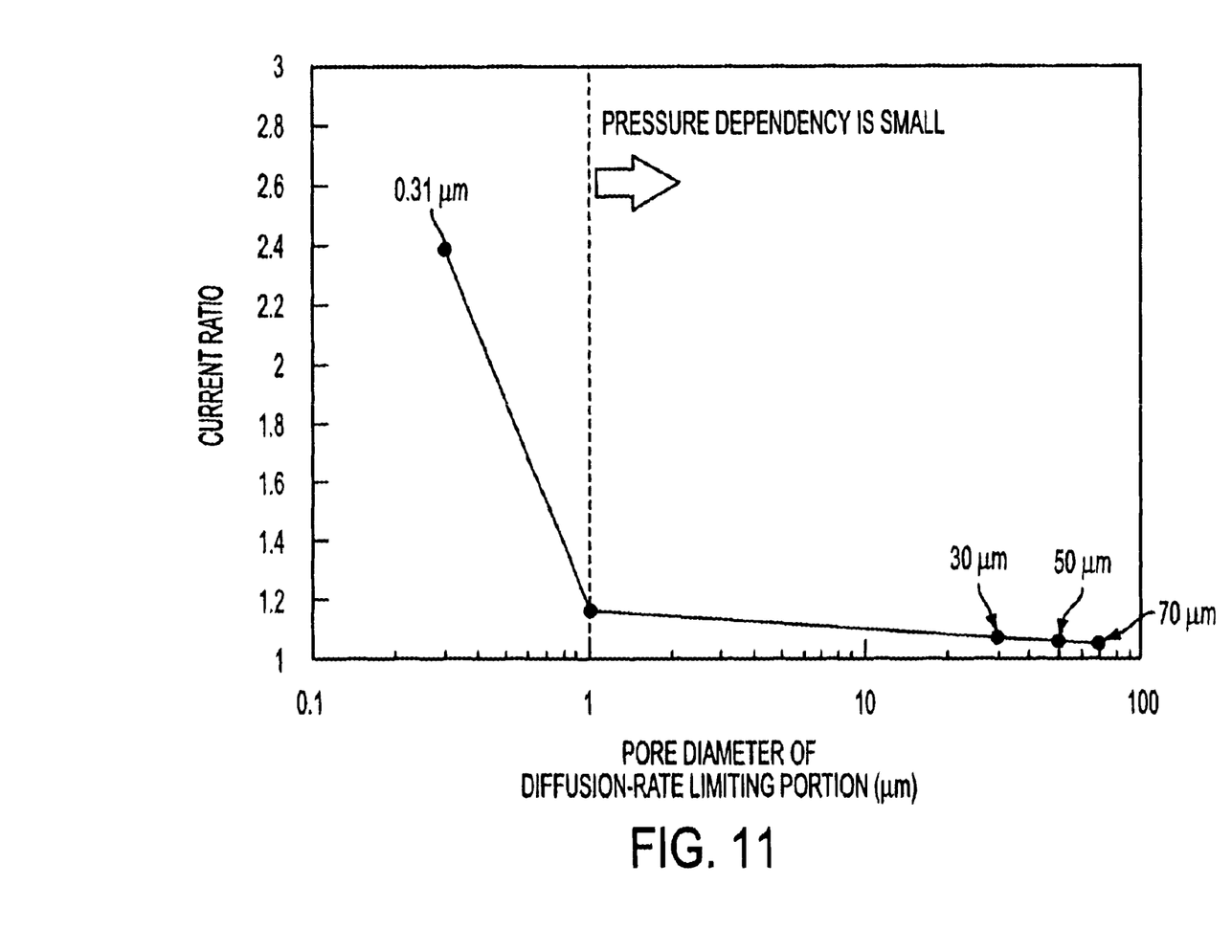
FIG. 11 is a graph in relation to measurement 6, showing the relationship between gas pressure and current (current flowing between the first and second electrodes) measured for each of different pore diameters of the diffusion-rate limiting portion.

Potential difference between first electrode and reference electrode (control target): 150 mV; and Constant current for self-generation reference electrode: 10 $\mu$A FIG. 11 is a graph provided for describing results of measurement 6 and showing the current ratio (relative ratio of current flowing between the first and second electrodes) obtained by changing the gas pressure. As is understood from FIG. 11, the gas pressure dependency decreases greatly when the pore diameter (opening diameter) of the diffusion-rate limiting portion is 1 $\mu$m or greater.

The present invention provides a hydrogen gas sensor capable of accurately measuring hydrogen concentration in the presence of a variety of interfering gasses. Further, use of the hydrogen gas sensor of the present invention enables accurate measurement of hydrogen concentration of a fuel gas used for polymer electrolyte fuel cells.

Having described specific preferred embodiments of the present invention, it is to be understood that the invention is not limited to those precise embodiments, and that various changes and modifications may be effected therein by one skilled in the art without departing from the scope of the invention as defined in the appended claims.

This application is based on Japanese Patent Application No. Hei. 11-333422 filed Nov. 24, 1999 which is incorporated herein by reference in its entirety.

What is claimed is:

1. A hydrogen gas sensor comprising:
   a proton-conductive layer formed of a polymer electrolyte;
   first and second electrodes provided in contact with the proton-conductive layer;
   a diffusion-rate limiting portion disposed between the first electrode and an atmosphere of a gas under measurement containing hydrogen; and
   a circuit for applying a voltage between the first and second electrodes such that hydrogen introduced from the atmosphere via the diffusion-rate limiting portion undergoes dissociation, decomposition, or reaction to produce protons on the first electrode, and for determining the hydrogen concentration of the gas under measurement based on a saturation current which flows as a result of conduction of protons from the first electrode to the second electrode via the proton-conductive layer,
   said sensor having a proton-conducting rate from the first electrode to the second electrode that is greater than a rate at which protons derived from hydrogen are introduced onto the first electrode via the diffusion-rate limiting portion, and
   the diffusion-rate limiting portion has a diffusion resistance and/or the first or second electrode has an area relative to the proton conductivity of the proton-conductive layer such that at a hydrogen concentration of the gas under measurement of up to 40% a ratio of saturation current flowing between the first and second electrodes at $H_2O=30\%$/saturation current flowing between the first and second electrodes at $H_2O=10\%$ falls within a range of 1 to 1.5, wherein the $H_2O$ content is the $H_2O$ content of the atmosphere of a gas under measurement.

2. The hydrogen gas sensor as claimed in claim 1, further comprising a solution containing a polymer electrolyte arranged at an interface between the proton-conductive layer and the first electrode and/or the second electrode.

3. The hydrogen gas sensor as claimed in claim 1, wherein the first and second electrodes are positioned in an opposed manner to sandwich the proton-conductive layer therebetween.

4. The hydrogen gas sensor as claimed in claim 1, wherein the gas-diffusion resistance of the diffusion-rate limiting portion is set such that current (a)>current (b):
   current (a) is a current flowing between the first and second electrodes upon application of a voltage of 50 mV or higher between the first and second electrodes in a state in which the gas-diffusion resistance of the diffusion-rate limiting portion is 0.9 mA/mm$^2$ or more with current conversion at $H_2=40\%$ and the measurement gas has a $H_2O$ concentration of 10% or less at 80° C. or a CO concentration of 1,000 ppm or greater;
   current (b) is a saturation current flowing between the first and second electrodes in a state in which the gas-diffusion resistance of the diffusion-rate limiting portion is less than 0.9 mA/mm$^2$ with current conversion at $H_2=40\%$ and the measurement gas has a $H_2O$ concentration of 15% or greater and a CO concentration of 800 ppm or less.

5. The hydrogen gas sensor as claimed in claim 1, for measurement of hydrogen concentration of a fuel gas for a polymer electrolyte fuel cell.

6. The hydrogen gas sensor as claimed in claim 1, wherein the diffusion-rate limiting portion has a gas diffusion resistance such that a saturation current flowing between the first and second electrodes at a $H_2O$ concentration of 15% or greater and a CO concentration of 800 ppm or less, is lower than a current which flows between the first and second electrodes, in the absence of a diffusion-rate limiting portion, or with a diffusion-rate limiting portion having a gas-diffusion resistance of 0.9 mA/mm$^2$ or more with current conversion at $H_2=40\%$ and a $H_2O$ concentration of 10% or less at 80° C. or a CO concentration of 1,000 ppm or greater.

7. The hydrogen gas sensor as claimed in claim 1, wherein the diffusion-rate limiting portion has a diffusion resistance and/or the first or second electrode has an area relative to the proton conductivity of the proton-conductive layer such that at any given hydrogen concentration of the gas under measurement a ratio of saturation current flowing between the first and second electrodes at CO=1000 ppm/saturation current flowing between the first and second electrodes at CO=0 ppm falls within a range of 0.9 to 1.

8. The hydrogen gas sensor as claimed in claim 1, wherein the proton-conductive layer has a proton conductivity relative to a diffusion resistance of said diffusion-rate limiting portion such that the saturation current varies less than 5% when the $H_2O$ concentration of the gas under measurement is changed from 10% to 30%.

9. The hydrogen gas sensor as claimed in claim 1, wherein the diffusion-rate limiting portion comprises porous alumina ceramic having an average pore diameter of 1 $\mu$m or higher.

10. The hydrogen gas sensor as claimed in claim 1, wherein the diffusion-rate limiting portion comprises dense alumina ceramic having through-holes having an opening diameter of 30 $\mu$m or higher.

11. A hydrogen gas sensor comprising:
a proton-conductive layer formed of a polymer electrolyte;
first and second electrodes and a reference electrode provided in contact with the proton-conductive layer;
a diffusion-rate limiting portion disposed between the first electrode and an atmosphere of a gas under measurement containing hydrogen; and
a circuit for applying a voltage between the first and second electrodes such that a constant voltage develops between the first electrode and the reference electrode, and such that hydrogen gas introduced from the atmosphere via the diffusion-rate limiting portion undergoes dissociation, decomposition, or reaction to produce protons on the first or second electrode, and for detecting the hydrogen concentration of the gas under measurement based on a saturation current which flows as a result of conduction of protons via the proton-conductive layer,
said sensor having a proton-conducting rate from the first electrode to the second electrode that is greater than a rate at which protons derived from hydrogen are introduced onto the first electrode via the diffusion-rate limiting portion, and
the diffusion-rate limiting portion has a diffusion resistance and/or the first or second electrode has an area relative to the proton conductivity of the proton-conductive layer such that at a hydrogen concentration of the gas under measurement of up to 40% a ratio of saturation current flowing between the first and second electrodes at $H_2O$=30%/saturation current flowing between the first and second electrodes at $H_2O$=10% falls within a range of 1 to 1.5, wherein the $H_2O$ content is the $H_2O$ content of the atmosphere of a gas under measurement.

12. The hydrogen gas sensor as claimed in claim 11, further comprising a solution containing a polymer electrolyte arranged at an interface between the proton-conductive layer and the first electrode and/or the second electrode.

13. The hydrogen gas sensor as claimed in claim 11, wherein the first and second electrodes are positioned in an opposed manner to sandwich the proton-conductive layer therebetween.

14. The hydrogen gas sensor as claimed in claim 11, wherein the gas-diffusion resistance of the diffusion-rate limiting portion is set such that current (a)>current (b):
current (a) is a current flowing between the first and second electrodes upon application of a voltage of 50 mV or higher between the first and second electrodes in a state in which the gas-diffusion resistance of the diffusion-rate limiting portion is 0.9 mA/mm$^2$ or more with current conversion at $H_2$=40% and the measurement gas has a $H_2O$ concentration of 10% or less at 80° C. or a CO concentration of 1,000 ppm or greater;
current (b) is a saturation current flowing between the first and second electrodes in a state in which the gas-diffusion resistance of the diffusion-rate limiting portion is less than 0.9 mA/mm$^2$ with current conversion at $H_2$=40% and the measurement gas has a $H_2O$ concentration of 15% or greater and a CO concentration of 800 ppm or less.

15. The hydrogen gas sensor as claimed in claim 11, for measurement of hydrogen concentration of a fuel gas for a polymer electrolyte fuel cell.

16. The hydrogen gas sensor as claimed in claim 11, wherein the diffusion-rate limiting portion has a gas diffusion resistance such that a saturation current flowing between the first and second electrodes at a $H_2O$ concentration of 15% or greater and a CO concentration of 800 ppm or less, is lower than a current which flows between the first and second electrodes, in the absence of a diffusion-rate limiting portion, or with a diffusion-rate limiting portion having a gas-diffusion resistance of 0.9 mA/mm$^2$ or more with current conversion at $H_2$=40% and a $H_2O$ concentration of 10% or less at 80° C. or a CO concentration of 1,000 ppm or greater.

17. The hydrogen gas sensor as claimed in claim 11, wherein the diffusion-rate limiting portion has a diffusion resistance and/or the first or second electrode has an area relative to the proton conductivity of the proton-conductive layer such that at any given hydrogen concentration of the gas under measurement a ratio of saturation current flowing between the first and second electrodes at CO=1000 ppm/ saturation current flowing between the first and second electrodes at CO=0 ppm falls within a range of 0.9 to 1.

18. The hydrogen gas sensor as claimed in claim 1, wherein the proton-conductive layer has a proton conductivity relative to a diffusion resistance of said diffusion-rate limiting portion such that the ratio of saturation current at an $H_2O$ concentration of 30% of the gas under measurement to an $H_2O$ concentration of 10% of the gas under measurement is about 1.041 or less.

19. The hydrogen gas sensor as claimed in claim 11, wherein the diffusion-rate limiting portion comprises porous alumina ceramic having an average pore diameter of 1 $\mu$m or higher.

20. The hydrogen gas sensor as claimed in claim 11, wherein the diffusion-rate limiting portion comprises dense alumina ceramic having through-holes having an opening diameter of 30 $\mu$m or higher.

* * * * *

UNITED STATES PATENT AND TRADEMARK OFFICE
CERTIFICATE OF CORRECTION

PATENT NO.       : 6,652,723 B1                                         Page 1 of 1
APPLICATION NO. : 09/716225
DATED            : November 25, 2003
INVENTOR(S)      : Norihiko Nadanami et al.

It is certified that error appears in the above-identified patent and that said Letters Patent is hereby corrected as shown below:

Title Page
Under (75)   Inventors:   Norihiko Nadanami, Aichi (JP)
                          ~~Norobu Ishida~~ Noboru Ishida, Gifu (JP)
                          Takafumi Oshima, Aichi (JP)
                          Ryuji Inoue, Gifu (JP)
                          Tomonori Kondo, Aichi (JP)

Signed and Sealed this

Eleventh Day of December, 2007

JON W. DUDAS
*Director of the United States Patent and Trademark Office*